US006177073B1

(12) United States Patent
Zhang et al.

(10) Patent No.: US 6,177,073 B1
(45) Date of Patent: Jan. 23, 2001

(54) AGGREGATION PHEROMONE FOR THE ASIAN LONGHORNED BEETLE, *ANOPLOPHORA GLABRIPENNIS* (COLEOPTERA: CERAMBYCIDAE)

(75) Inventors: Aijun Zhang, Silver Spring; James E. Oliver, Laurel; Jeffrey R. Aldrich, Adelphi, all of MD (US)

(73) Assignee: The United States of America as represented by the Secretary of the Agriculture, Washington, DC (US)

( * ) Notice: Under 35 U.S.C. 154(b), the term of this patent shall be extended for 0 days.

(21) Appl. No.: 09/347,907

(22) Filed: Jul. 7, 1999

(51) Int. Cl.[7] .......................... A01N 35/00; A01N 35/02; A01N 31/00; A01N 31/02
(52) U.S. Cl. .......................... 424/84; 514/693; 514/715; 514/723; 514/724
(58) Field of Search ..................................... 568/496, 678; 424/84; 514/693, 722, 715, 723

(56) References Cited

U.S. PATENT DOCUMENTS

| 2,504,407 | * | 4/1950 | Gresham | 568/678 |
| 4,029,710 | * | 6/1977 | Suzuki | 568/465 |

OTHER PUBLICATIONS

Chemical Abstracts 88:120564, STN online version, 1977.*
Voerman, S. et al., "Sex pheromones of summer fruit Tortrix moth, Adoxophyes orana . . . ", Environmental Entomology, vol. 2, No. 5, pp. 751–756, Oct. 1973.*
Boyer et al., "Identification and synthesis of vesperal, the female sex pheromone of the longhorn beetle *Vesperus xatarti*", *Bull. Soc. Chim. Fr.*, vol. 134, pp. 757–764, 1997.
Leal et al., "Female sex pheromone of the longhorn beetle *Migdolus fryanus* Westwood: N–(2′S)–methylbutanoyl 2–methylbutylamine", *Experientia*, vol. 50, pp. 853–856, 1994.
Leal et al., "Structure, stereochemistry, and thermal isomerization of the male sex pheromone of the longhorn *Anaglyptus subfasciatus*", *Proc. Natl. Acad. Science*, vol. 92, pp. 1038–1042, 1995.
Schroder et al., "Synthesis of (3R)–3–Hydroxy–2–hexanone, (2R,3R)–2,3–Hexanediol and (2S,3R)–2,3–Hexanediol, the Male Sex Pheromone of *Hylotrupes bajulus* and *Pyrrhidium sanguineum* (Cerambycidae)", *Liebigs Ann. Chem.*, pp. 1211–1218, 1994.
Qiao Wang, "Evidence for a Contact Female Sex Pheromone in *Anoplophora Chinensis* (Forster) (Coleoptera: Cerambycidae Laminae)", *The Coleopterists Bulletin*, vol. 52(4), pp. 363–368, 1998.
Sakai et al., "Isolation and Identification of the Male Sex Pheromone of the Grape Borer *Xylotrechus pyrrhoderus* Bates (Coleoptera: Cerambycidae)", *Chemistry Letters*, pp. 263–264, 1984.

* cited by examiner

*Primary Examiner*—John Pak
(74) *Attorney, Agent, or Firm*—M. Howard Silverstein; John D. Fado; Janelle S. Graeter

(57) ABSTRACT

Compositions and methods are provided for attracting and subsequently trapping and/or killing adults of the Asian longhorned beetle, *Anoplophora glabripennis*, or interfering with their reproduction. The aggregation pheromones, 4-(n-heptyloxy)butanal and 4-(n-heptyloxy)butan-1-one, in combination with a trap or toxicant, provide means for monitoring, killing or inhibiting the reproduction of these insects.

4 Claims, 7 Drawing Sheets

AGGREGATION PHEROMONE FOR THE ASIAN LONGHORNED BEETLE, *ANOPLOPHORA GLABRIPENNIS* (COLEOPTERA: CERAMBYCIDAE)

BACKGROUND OF THE INVENTION

1. Field of the Invention

*Anoplophora glabripennis*, known as the Asian longhorned beetle (ALB), is a serious pest of pulp wood (poplars) and related trees (willow, elm and maple) in China, its native habitat. Other Anoplophora species endemic to southeast Asia (e.g. *A. malasiaca* and *A. chinensis*) are important pests of citrus tree crops. Control of the ALB in China currently relies on cutting down infested trees in an effort to restrict the spread of infestations. However, a significant amount of green untreated wood infested with larvae of the ALB and other wood-boring insect species has been used to construct pallets, crates and shoring materials used in the shipment of international cargo. This practice has resulted in worldwide dispersal of the ALB and other species, in view of China's participation in international trade.

This invention relates to compositions and methods useful for attracting, trapping and/or killing the adults of these wood-boring pests, or for interfering with their reproduction.

2. Description of the Related Art

Larvae of the Cerambycidae are known to burrow into the tissues of woody plants whose conditions range from dead and decomposing to alive and healthy. The family includes at least nine subfamilies totaling more than 35,000 species. The Asian longhorned beetle is a member of the largest and one of the most advanced subfamilies, the Lamiinae, whose species usually attack living trees.

In 1996 and 1998, established populations of the ALB were found in suburban areas of New York City and Chicago. These infestations were probably initiated several years ago, making it likely that other infestations remain to be found in the United States. If unchecked, the ALB could decimate susceptible deciduous trees throughout eastern North America. Therefore, State and Federal action agencies have launched intensive eradication programs in areas where established ALB populations have been found. These efforts, however, rely on the visual detection of adult beetles or on signs of their emergence from trees and, at best, may detect only 30% of the infested trees.

Inspection of cargo at points of entry into the U.S. and other countries has also been intensified, yet inspectors rely on visual inspection and, for logistical reasons, only a fraction of the wood packing materials are actually examined.

Behavioral evidence for the most primitive cerambycid subfamily (Prioninae) suggests that females attract males with pheromones, but for the more advanced subfamilies either sex may produce an attractant pheromone. Males of *Anaglyptus subfasciatus, Hylorupes jajulus, Pyrrhicium sanguineum*, and *Xylotrechus pyrrhoderus* (Cerambycinae) release particular blends and stereoisomers of 3-hydroxy-2-hexanone, 3-hydroxy-2-octanone, 2,3-hexanediol, and 2,3-octanediol from epidermal glands located on the pronotum of the beetles (Leal et al. 1995. *Proc. Natl. Acad. Sci. USA*. vol. 92, pp. 1038–1042; Sakai et al. 1984.*Chem. Letters*. pp. 263–264; Schröder et al. 1994. *Liebigs Ann. Chem.* pp. 1211–1218). These pheromones are attractive to females and, in some cases, males of the species. Attractant pheromones have been identified from females of two cerambycids species: *Migdolus fryanul* (Anoploderminae) females produce N-(2'S)-methylbutanoyl 2-methylbutylamine; female *Vesperus xatarti* (Vesperinae) produce 10-oxoisopiperitenone and 10-hydroxyisopiperitenone (Boyer et al. 1997. *Bull. Soc. Chim. Fr.* vol. 134, pp. 757–764; Leal et al. 1994. *Experientia*. vol. 50, pp. 853–856). In these species the females are wingless and attract males with pheromone. For *Anaplophora chinensis* there is evidence that the mating behavior of males is stimulated by a contact female sex pheromone occurring on her body surface (Wang, Q. 1998. *The Coleopterists Bull.* vol. 52, pp. 363–368).

Asian longhorned beetle pheromones have not been previously described; however, the need clearly exists for effective chemically-baited traps for the detection and control of ALB breeding populations.

SUMMARY OF THE INVENTION

We have discovered and subsequently isolated and synthesized Asian longhorned beetle pheromones which serve as effective attractants for the beetles.

In accordance with this discovery, it is an object of the invention to provide the novel pheromones for Asian longhorned beetles, 4-(n-heptyloxy)butanal and 4-(n-heptyloxy)butan-1-ol.

It is another object of the invention to provide bioactive compositions comprising at least one Asian longhorned beetle pheromone effective as an attractant for Asian longhorned beetles.

It is also an object of the invention to provide a method for attracting Asian longhorned beetles by exposing the beetles to a composition comprising at least one Asian longhorned beetle pheromone.

Other objects and advantages of the invention will become readily apparent from the following description.

DETAILED DESCRIPTION OF THE INVENTION

Aggregation pheromones in general are useful as attractants for insects from which the pheromones are derived. Functionalized ethers represented by the following formula are believed to have bioactivity for Anoplophora species:

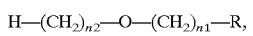

$$H-(CH_2)_{n2}-O-(CH_2)_{n1}-R,$$

where $R=CH_2OH$ or $CHO$, $n_1$=3–7, and $n_2$=1–9.

Accordingly, compositions containing these pheromones would be advantageous in efforts to control significant pests such as ALB. Efforts were thus made to identify and isolate pheromones from ALB, followed by tests to confirm the expected activity.

Figure 1:
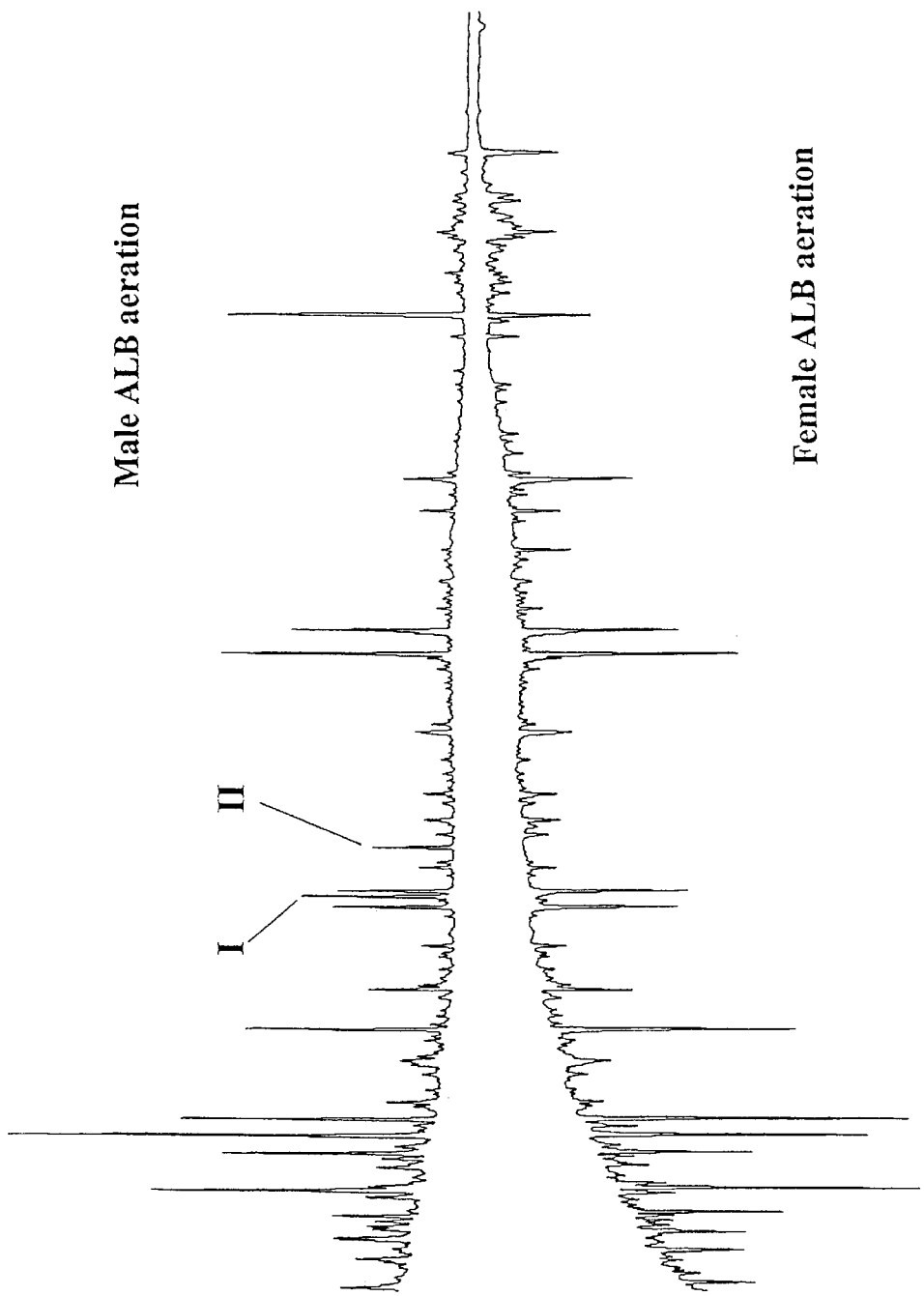
FIG. 1 shows reconstructed gas chromatograms of an aeration extract of male (top) versus female (bottom) Asian longhorned beetle (6 beetles of each, 24 hours) on a HP-5 capillary column. Two male specific compounds were marked as "I" and "II".
Figure 2:
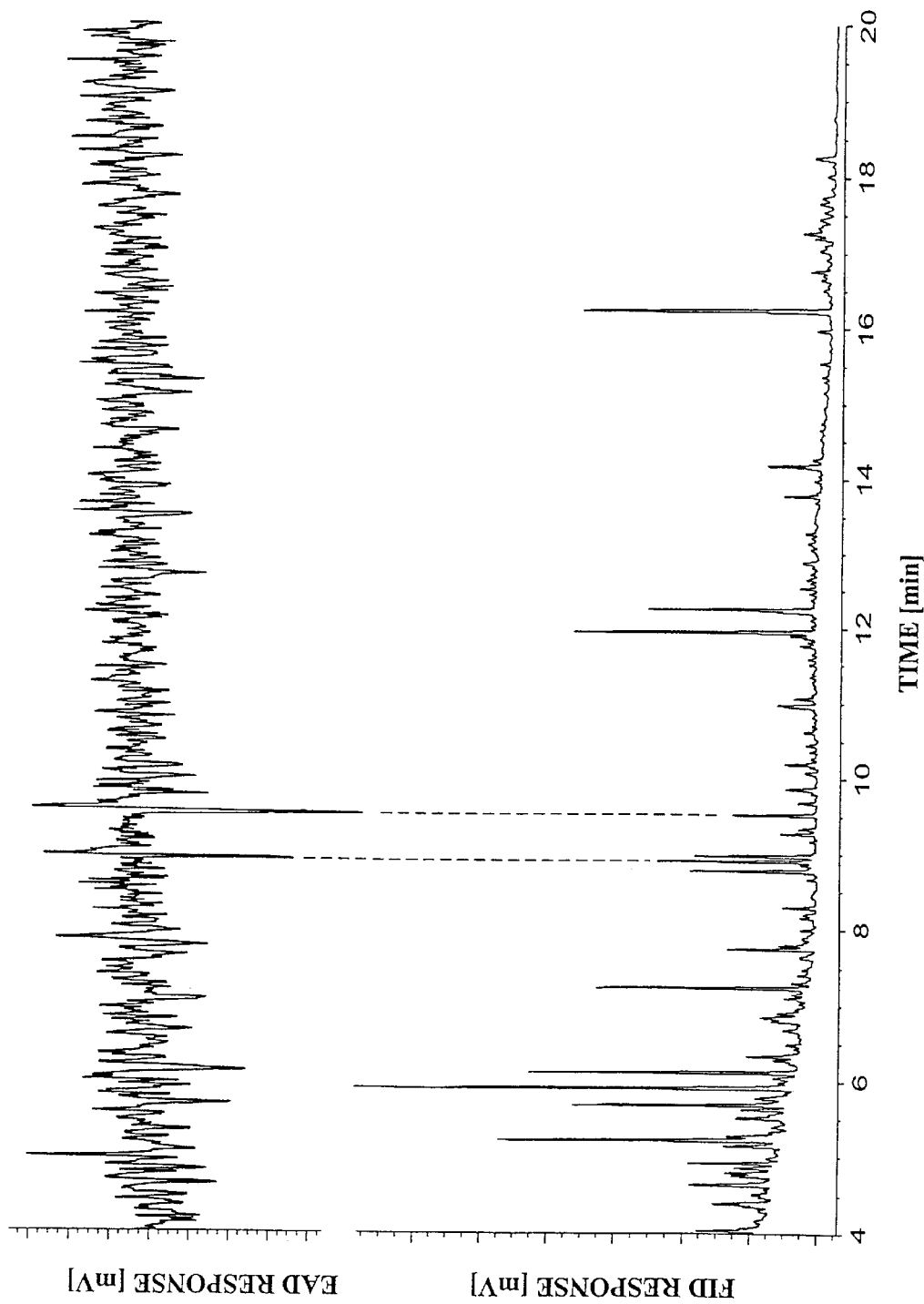
FIG. 2 shows the simultaneous responses of flame ionization detection (FID) and electroantennographic detection (EAD) of an adult male ALB to the volatiles of male ALB on a HP-5 capillary column.
Figure 3A:
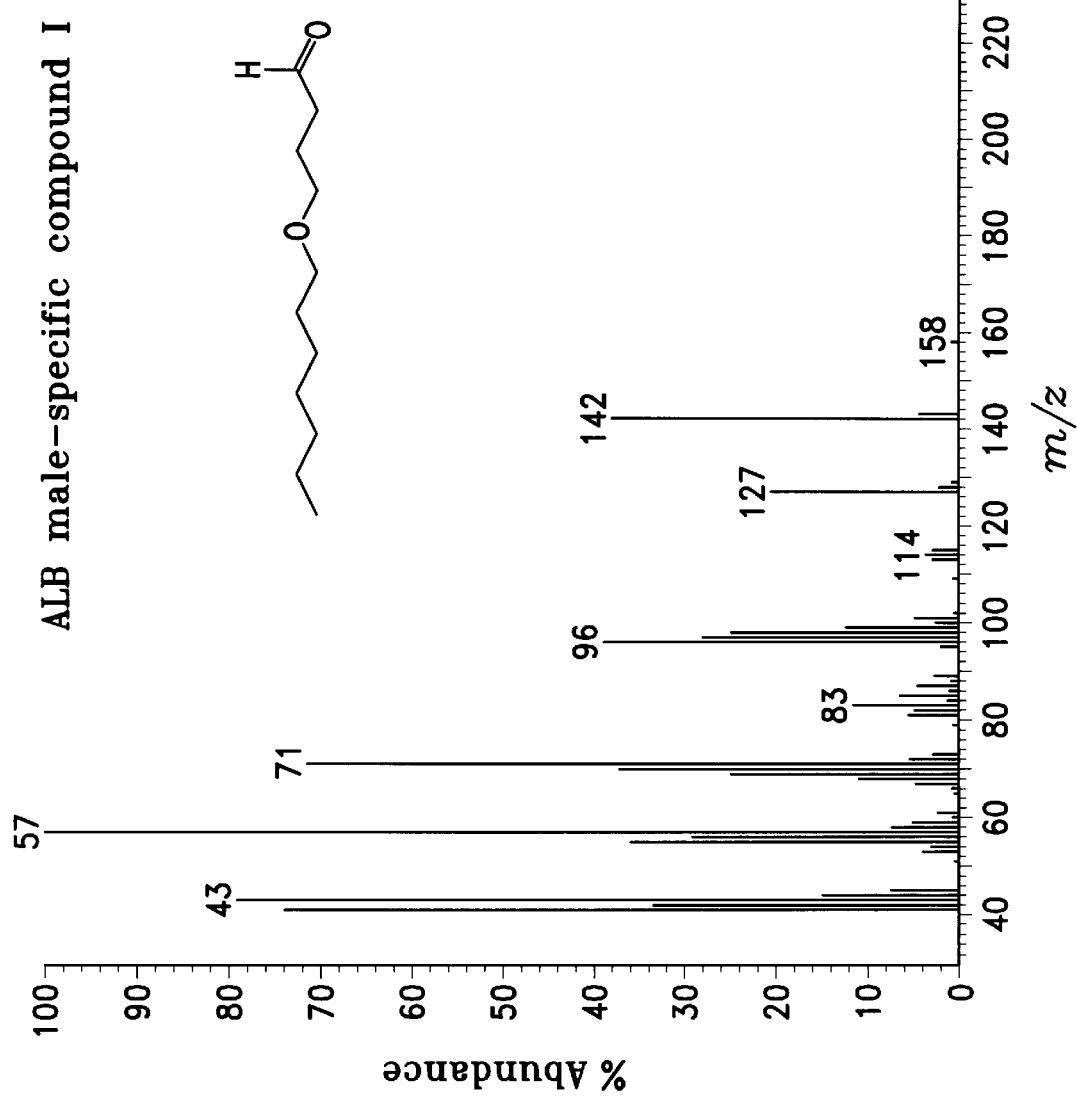
FIG. 3 shows the electron impact mass spectra of the synthetic pheromones (panels A and C) and the natural products (panels B and D) isolated from the aeration of 10-day-old ALB males.
Figure 3B:
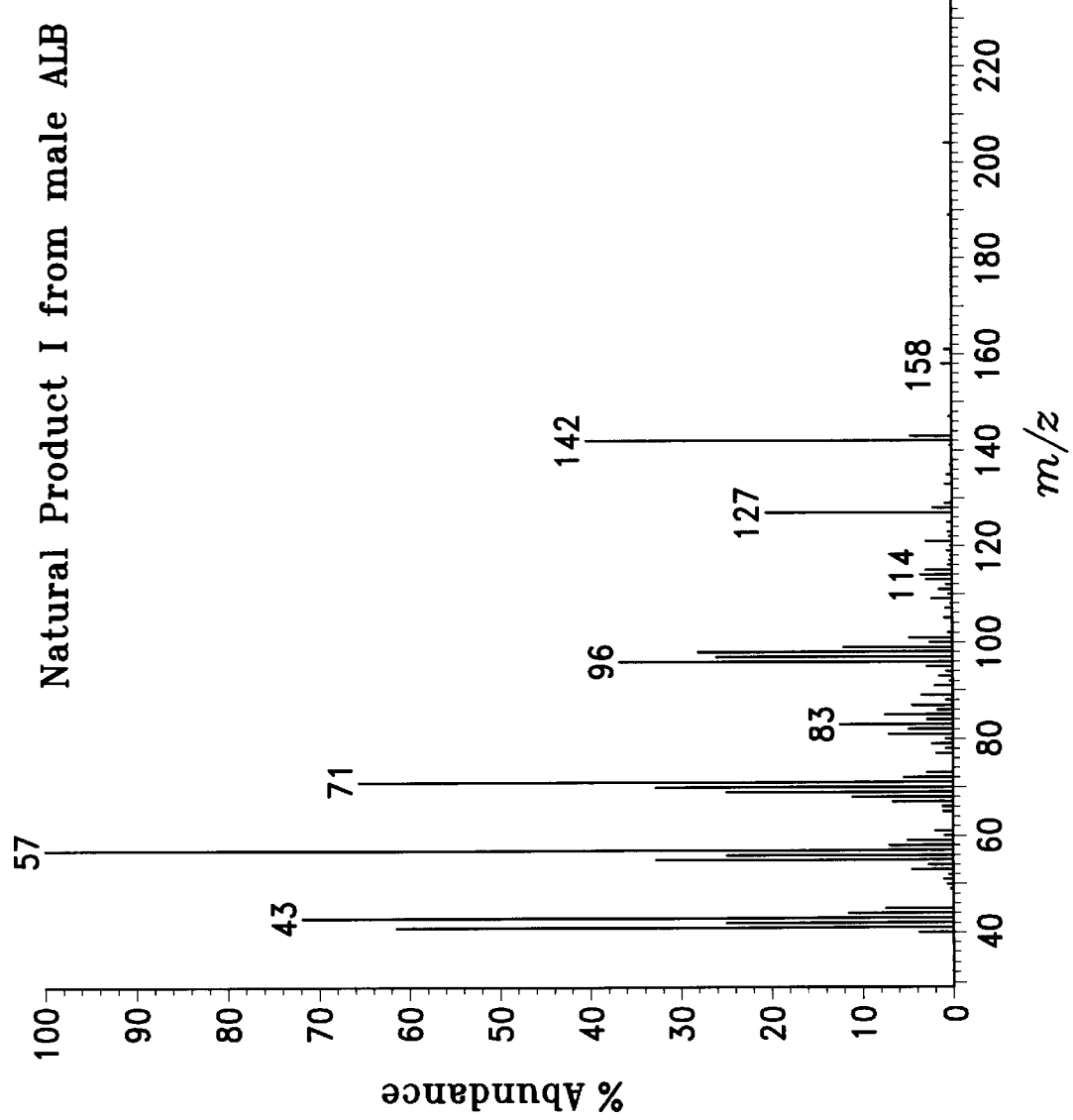
Figure 3C:
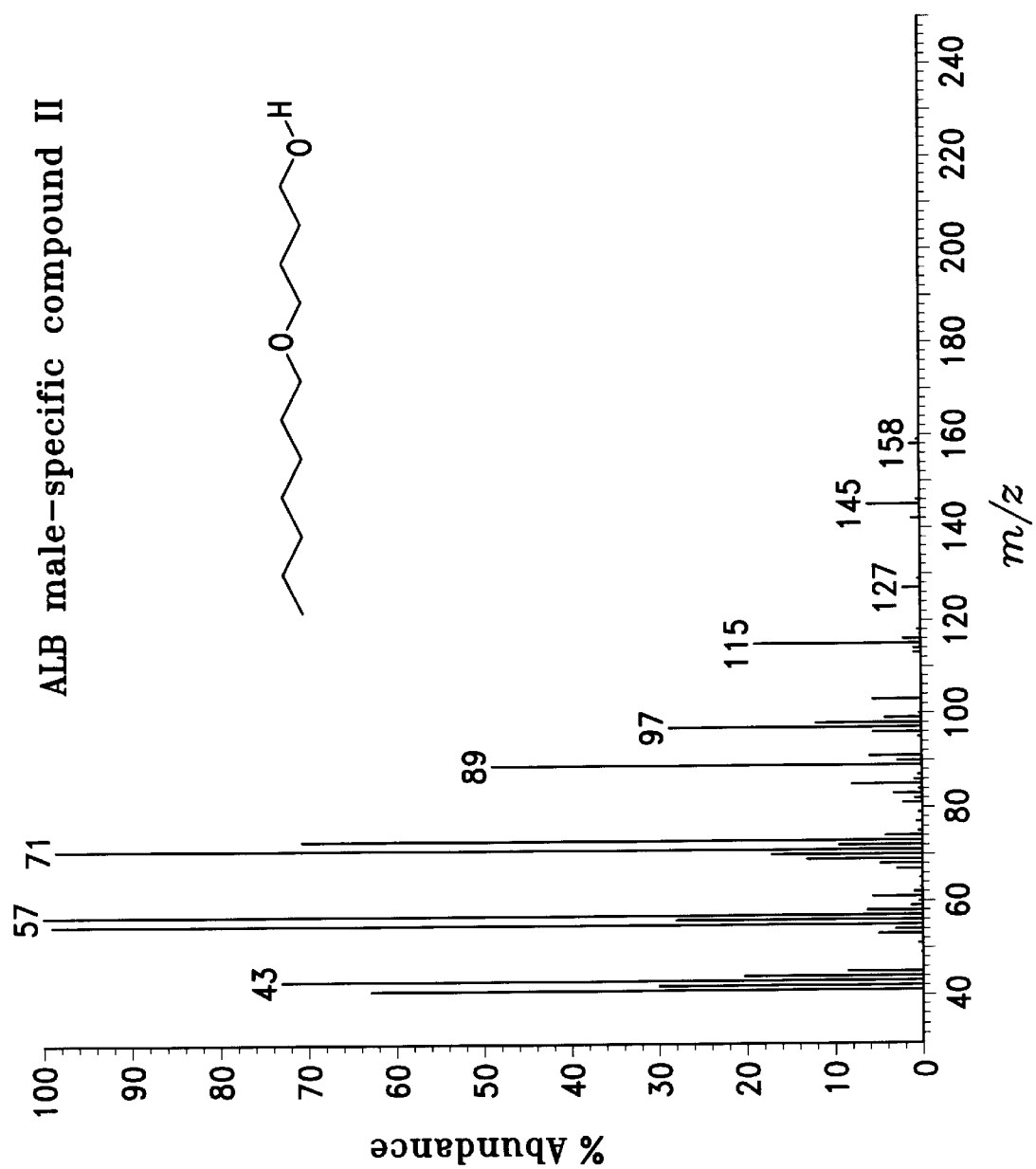
Figure 3D:
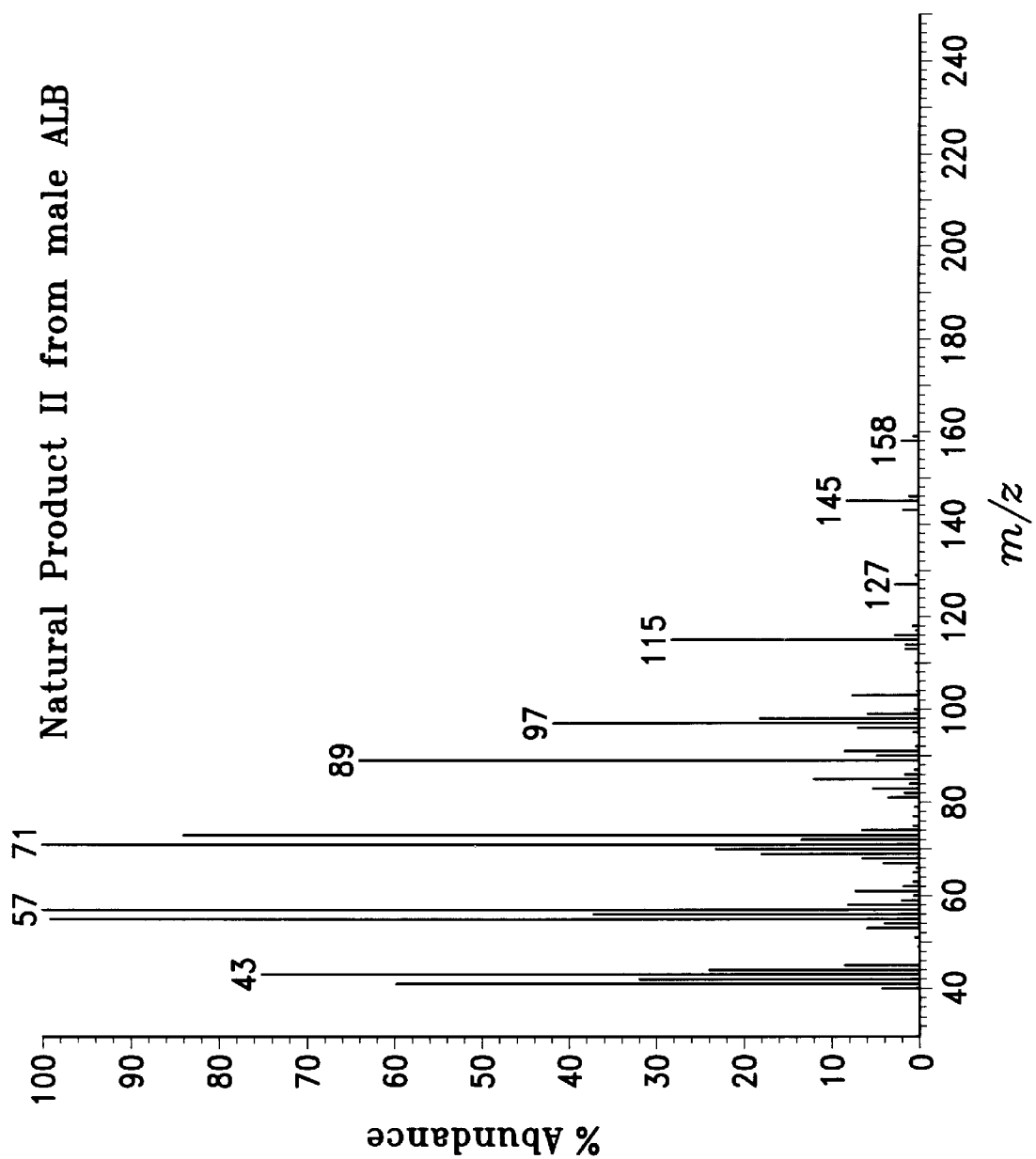

Initial experiments were carried out to isolate pheromone by aeration extraction (as described in Example 1). These extracts were obtained from *A. glabripennis* adults which emerged from logs cut down in Chicago infestation sites and transported to the quarantine facility of the Animal and Plant Health Inspection Service (APHIS) in Otis, Mass. Extracts were subsequently analyzed by the gas chromatography-electroantennographic detector technique (GC-EAD), and GC-mass spectrometry (GC-MS). Comparison of aeration extracts from males and from females revealed that males produced two compounds not detected from females (see FIG. 1, compounds I and II). GC-EAD recordings using antennae from ALE males (FIG. 2) and females (not shown) demonstrated that the insects were especially sensitive to the two male-specific compounds.

The chemical structures of the two compounds were postulated based on mass spectral data. In addition, molecular weights were determined to be 186 amu and 188 amu for compounds I and II, respectively (see Example 3). The data indicated that compound II had an exchangeable proton resulting from the presence of an hydroxyl moiety (—OH) in the molecule. They also suggested that compound I was analogous to compound II, but with an oxygen in a higher oxidation state than that of the corresponding hydroxyl oxygen in compound I.

Figure 4:
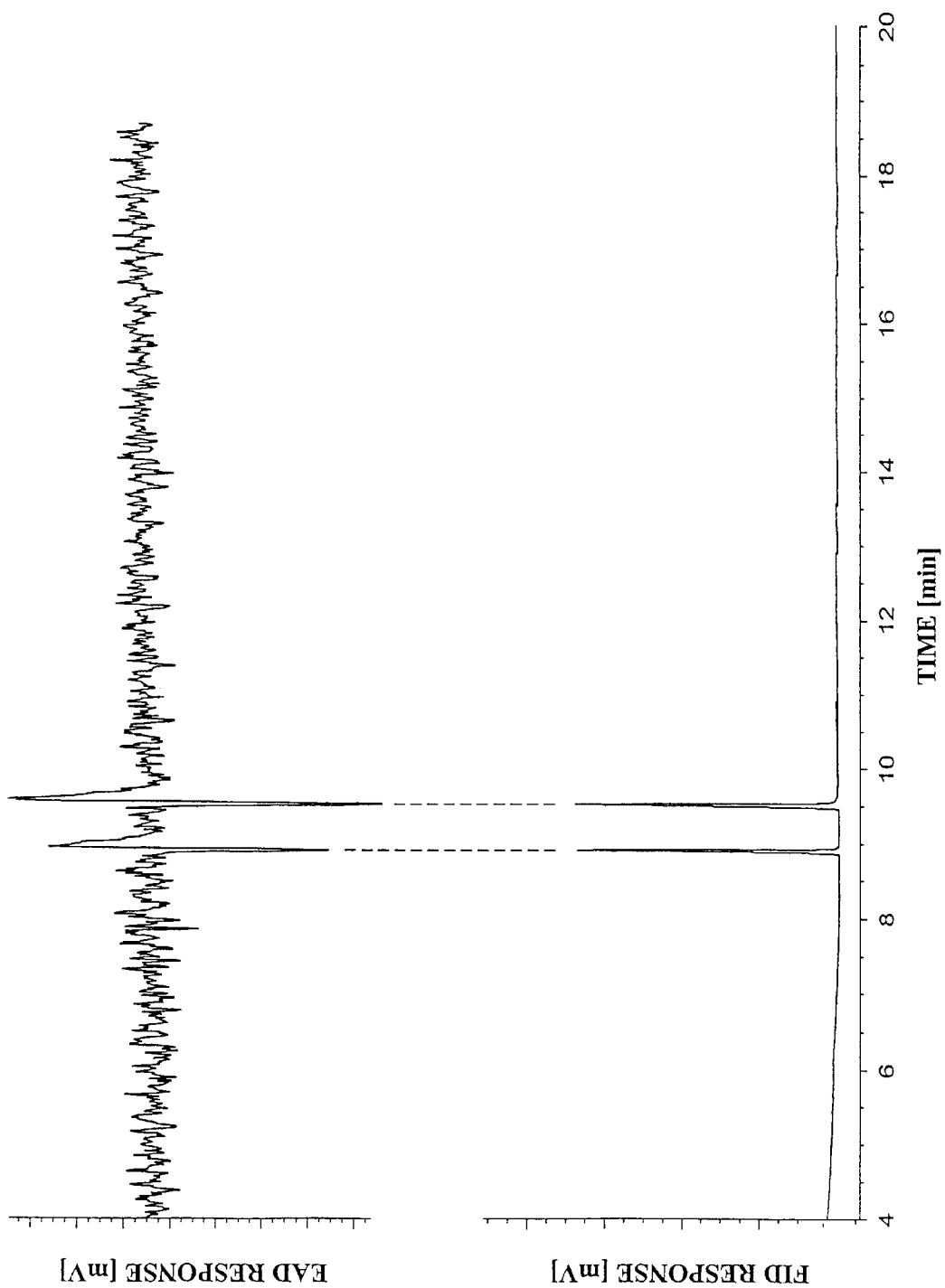
FIG. 4 shows the simultaneous responses of FID and EAD of an adult male ALB to a mixture of synthetic ALB aggregation pheromone on a HP-5 capillary column.

The expected compounds were then synthesized (as described in Examples 4 and 5) and their chromatographic and spectral data compared to those of the beetle-derived compounds. As seen in FIG. 3, panels C and D, the data for synthetic compound II matched those for natural product II and confirmed that male ALB produce the compound 4-(n-heptyloxy)butan-1-ol (hereinafter compound II). As expected, oxidation of synthetic compound II to the corresponding 4-(n-heptyloxy)butanal resulted in a novel compound identical to that of natural product I, as shown in FIG. 3, panels A and B. GC-EAD experiments also demonstrated that both male (FIG. 4) and female (not shown) ALB antennae were highly responsive to both synthetic compounds I and II.

Further experimentation was carried out to confirm that compounds I and II had pheromone activity and were effective attractants for ALE (see Example 6). Tests carried out in a wind tunnel resulted in insect flight as a result of simultaneous exposure to both compounds I and II. Results are shown in Table I. Similar prior tests using synthetic plant volatiles and other suspected pheromone compounds failed to elicit any movement by the beetles.

TABLE 1

Attraction of 7-day-old adult Asian longhorned beetles to a 1:1 blend of synthetic I and II (100 µg each) in a wind tunnel at the Otis, MA quarantine laboratory.

| Insect | Day | Response* |
|--------|-----|-----------|
| Male #1 | 1 | 11 consecutive flights |
| Male #2 | 1 | 11 consecutive flights |
| Female #1 | 1 | Walked upwind |
| Male #1 | 2 | 11 consecutive flights |
| Male #2 | 2 | 6 consecutive flights |
| Female #2 | 2 | 11 consecutive flights |

*Test terminated after 11 flights

The pheromones may be utilized in applications well known to those of skill in the art. For example, a composition containing at least one of the compounds or a mixture of the two compounds and a suitable carrier is a useful bait for insect traps. Since eradication and interception efforts rely on detection of the beetles, efficient chemically-baited traps are key to containment efforts and to efforts to locate heretofore unknown pockets of infestation. In addition, mating disruption is a known effective means for insect control and may be achieved by saturating infested areas with pheromone-laced dispensers. The pheromones may also be utilized in combination with toxicants effective for killing insects by, for example, placing both pheromone bait and toxicant in a trap where insects may first be attracted by the bait, then killed by the toxicant.

Suitable carriers are also well-known in the art and are selected in accordance with the ultimate application of interest. Agronomically acceptable substances are of particular interest and include aqueous solutions, glycols, alcohols, ketones, esters, hydrocarbons and halogenated hydrocarbons. Polyvinyl chloride is a carrier of particular interest. In addition, solid carriers such as clays, cellulosic and rubber materials and synthetic polymers are of interest.

The amounts of pheromone utilized in the composition vary according to the ultimate use and the carrier of choice. For example, an amount effective for attracting beetles may easily be determined by those of skill in the art by combining pheromone and carrier and determining at what level the bait is effective (using criteria such as that described in Example 6 and shown in Table 1).

In one embodiment, the attractant may be used to monitor the presence of pests in an area, or to concentrate the pests on certain trees where they could be economically destroyed by limited insecticide application. In another embodiment, the habitat be be saturated with the synthetic pheromone compounds during the flight (mating) period of the beetles, thereby inhibiting mate-finding and leading to suppression or elimination of the pest population in an area.

The following examples are intended only to further illustrate the invention and are not intended to limit the scope of the invention as defined by the claims.

EXAMPLES

Example 1

Isolation of Asian Longhorned Beetle Pheromone

Aeration extracts were prepared by confining groups of 5–10 male or 5–10 female ALBs in a 1 L glass chamber for several days, sometimes with twigs of Norway maple (*Acer platanoides*). Air was drawn into the apparatus by vacuum (~1 L/min) through an activated charcoal filter (6–14 mesh, 2 cm×1.5 cm OD; Fisher Scientific) in two openings to remove contaminating volatiles and, after passing over the beetles, the volatile natural products were trapped as air exited through two separate columns (15 cm×0.6 cm OD) packed with an adsorbent polymer (Super Q, 200 mg each; Alltech Associates, Inc.). Super Q traps were changed every 24 hr, the airborne volatiles were eluted with four portions of GC-grade methylene chloride (0.5 mL/each), and extracts were stored at −4° C. for further analyses.

Example 2

Chemical Analysis & Electrophysiological Recordings

Aeration extracts were analyzed by the gas chromatography-electroantennographic detector technique (GC-EAD), and GC-mass spectrometry (GC-MS) in the electron impact (EI) and chemical ionization (CI) modes. Hewlett Packard instrumentation was used (5890 and 6890 GCs for the GC-EAD and GC-EI-MS, respectively), and Finnigan instrumentation was used for GC-CI-MS. All GC analyses were performed with 60 m capillary columns (either DB-5™ or DB-WAXetr™, 0.25-mm ID, 0.25-μm film thickness; J&W Scientific). Nitrogen was the carrier gas for the GC-EAD systems; helium was the carrier gas for GC-MS. The standard temperature program was from 50° C. for 2 min, to 250° C. at 15° C./min, and holding for 10 min, with injector and detector temperatures at 250° C. Identical GC-EAD equipment was assembled in two laboratories: one was used with antennae from ALB males and the other used with antennae from ALB females and males. The GC-EAD systems were constructed by splitting the column effluent, adding nitrogen makeup gas at the splitter (modified VSIS-5 inlet splitter; SGE, Inc.), with one-half of the effluent going to the flame ionization detector (FID) of the GC and the other half of the effluent passing to the EAD.

The antennal preparation consisted of an acrylic holder with two saline-filled (0.9% NaCl) wells into which the ends of the antennae were introduced. A gold wire was inserted into each well, and these electrical leads were connected by a short coaxial cable to a high-impedance 1:100 amplifier with automatic baseline drift compensation. The antennal preparation was cooled to ~40° C. by inserting the acrylic holder into a water-cooled condenser mounted on top of the GC. The split effluent from the GC passed through a hole in the bottom of the condenser 1 cm in front of the antenna, and was flushed over the antenna by an airstream (500 mL/min) entering the opposite end of the condenser. The outputs from the FID and the EAD were displayed and recorded with a computer using HP ChemStation software.

Example 3
Pheromone Identification

The electrophysiologically active male-specific compounds were identified by their mass spectra, followed by synthesis of standards verifying the structures postulated for the natural products. The mass spectra of the natural products (FIGS. 3 B&D) did not match spectra of known compounds in the HP computerized database or in the literature. The CI-MS of compounds I and II using ammonia ($NH_3$) as the reagent gas produced prominent ions at m/z 187 and 204, and 189 and 206 ($[M+H]^+$ and $[M+NH_4]^+$), indicating molecular weights (MW) of 186 and 188, respectively. The CI-MS of I and II using deuteroammonia ($ND_3$) as the reagent gas produced prominent ions at 188 and 208 for compound I ($[M+D]^+$ and $[M+ND_4]^+$, and m/z 191 and 211 ($[M+2D-H]^+$ and $[M+ND_4-H+D]^+$). The deuteroammonia CI-MS data verified that the MW of compound I is 186 with no exchangeable protons, while the CI-MS data for compound II indicated that this compound has a MW=188 with one exchangeable proton resulting from the presence of an hydroxyl moiety (—OH) in the molecule. These data suggested that compound I was analogous to compound II, but with an oxygen in a higher oxidation state than that of the corresponding hydroxyl oxygen in compound I.

Example 4
Synthesis of Pheromone (Compound I)

A solution of oxalyl chloride (42 mL) in dry methylene dichloride (750 mL) was cooled under a nitrogen atmosphere to −75° C. Dimethylsulfoxide (72 mL) was added dropwise with stirring, followed after 10 minutes by a solution of 4-(n-heptyloxy)butan-1-ol (75.2 g from below) in methylene dichloride (75 mL). The mixture was stirred and allowed to warm to −45° C., then was again cooled to −75° C. and treated dropwise with triethylamine (292 mL). After the addition was complete, the cooling bath was removed and the mixture was allowed to slowly warm to room temperature and stir one hour. Ice was added, and the product was partitioned between water and methylene dichloride. The solvent was removed with a rotary evaporator, and the residue was dissolved in petroleum ether (500 mL) and the solution was rinsed in water, cold aqueous hydrochloric acid, water, and saturated aqueous sodium bicarbonate. After drying over magnesium sulfate, the solvent was stripped in vacuo, and the residue was distilled to give 57.6 g (77%) of 4-(n-heptyloxy)butanal, b.p. 60° C., 0.26 Torr.

Example 5
Synthesis of Pheromone (Compound II)

A solution of butan-1,4-diol (180 g, 2 mol) in dry N,N-dimethylformamide (1 L) was stirred under a nitrogen atmosphere and cooled with an ice bath while sodium hydride (60% in mineral oil, 76 g, 1.9 mol) was added in portions over about 10 minutes. The solution was then slowly heated to 60° C., then again cooled and a solution of 1-bromoheptane (190 mL, 1.21 mol) in dry tetrahydrofuran (200 mL) was added dropwise. After the addition, the solution was again heated until the temperature reached 60°–70° C., then was cooled and added to ice (1 kg). The mixture was extracted with ether-hexane (1:1, 3×200 mL), and the combined extracts were rinsed with water (2×200 mL) and finally with saturated sodium chloride solution (1×200 mL). After drying over magnesium sulfate, the solvent was removed with a rotary evaporator and the residue was distilled to give 156.6 g (69%) of compound II, b.p. 88°–91° C., 0.1 Torr.

Example 6
Behavioral Testing

Synthetic compounds I and II (FIGS. 3 A&C) were tested in a wind tunnel (40 cm×40 cm×150 cm) in the Otis, Mass., quarantine laboratory. The responses of 7-day-old adult males and females to the synthetic compounds applied to filter paper (100 μg each) at the upwind end of the chamber were recorded. After each flight, the beetle was retrieved and placed back at the downwind end of the chamber and held for 20–30 sec under a plastic cup before being allowed to respond again. A test was terminated when an individual beetle flew 11 consecutive times. The results of these tests are shown in Table 1. Prior tests conducted similarly in the wind tunnel using synthetic plant volatiles and other suspected pheromone compounds failed to elicit any movement by the beetles.

We claim:

1. A composition comprising at least one pheromone for Asian longhorned beetle in an amount effective for attracting said beetle and an agronomically acceptable carrier, wherein said pheromone has the formula

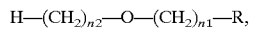

where R=$CH_2OH$ or CHO, $n_1$=3–7, and $n_2$=1–9.

2. The composition of claim 1, wherein said pheromone is 4-(n-heptyloxy)butanal, 4-(n-heptyloxy)butan-1-ol or a mixture thereof.

3. A method for attracting Asian longhorned beetles, said method comprising exposing said beetles to a composition comprising at least one pheromone for said beetles in an amount effective for attracting said beetles and an agronomically acceptable carrier, wherein said pheromone has the formula

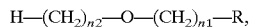

where R=$CH_2OH$ or CHO, $n_1$=3–7, and $n_2$=1–9.

4. The method of claim 3, wherein said composition comprises 4-(n-heptyloxy)butanal or 4-(n-heptyloxy)butan-1-ol or a mixture thereof and an agronomically acceptable carrier.

* * * * *